(12) United States Patent
Shakespeare et al.

(10) Patent No.: US 7,812,947 B2
(45) Date of Patent: Oct. 12, 2010

(54) APPARATUS AND METHOD FOR MEASURING AND/OR CONTROLLING PAPER PULP PROPERTIES

(75) Inventors: Tarja T. Shakespeare, Savo (FI); John F. Shakespeare, Savo (FI)

(73) Assignee: Honeywell International Inc., Morristown, NJ (US)

( * ) Notice: Subject to any disclaimer, the term of this patent is extended or adjusted under 35 U.S.C. 154(b) by 404 days.

(21) Appl. No.: 12/017,092

(22) Filed: Jan. 21, 2008

(65) Prior Publication Data

US 2009/0185162 A1 Jul. 23, 2009

(51) Int. Cl.
*G01J 3/30* (2006.01)
(52) U.S. Cl. ......................... 356/318; 356/317; 356/73; 356/51; 250/458.1; 250/459.1
(58) Field of Classification Search ................. 356/317, 356/318, 73, 51; 250/458.1, 459.1, 461.1
See application file for complete search history.

(56) References Cited

U.S. PATENT DOCUMENTS

| | | | | |
|---|---|---|---|---|
| 5,216,483 | A * | 6/1993 | Berthold et al. | 356/318 |
| 5,220,172 | A | 6/1993 | Berthold et al. | |
| 5,374,555 | A | 12/1994 | Pokora et al. | |
| 5,486,915 | A * | 1/1996 | Jeffers et al. | 356/318 |
| 5,953,111 | A * | 9/1999 | Millar et al. | 356/73 |
| 6,551,451 | B2 * | 4/2003 | Trung et al. | 162/49 |
| 2007/0153277 | A1 | 7/2007 | Shakespeare et al. | |
| 2010/0020168 | A1 * | 1/2010 | Ye | 348/92 |

FOREIGN PATENT DOCUMENTS

WO WO 84/00181 A1 1/1984

OTHER PUBLICATIONS

Robert L. Feller, "Comments on the Measurement of "Yellowness" in Pulp and Paper," The Book and Paper Group Annual, vol. Six 1987, The American Institute for Conservation, May 1987, 9 pages.
M. K. Ramasubramanian et al., "Optical Sensor for Noncontact Measurement of Lignin Content in High-Speed Moving Paper Surfaces," IEEE Sensors Journal, vol. 5, No. 5, Oct. 2005, pp. 1132-1139.

(Continued)

*Primary Examiner*—L. G Lauchman (57) ABSTRACT

A method includes illuminating a material using first light. The first light is associated with one or more ultraviolet wavelengths/wavelength bands, and the material includes pulp fibers. The method also includes measuring second light from the material, where the second light is based on the first light. The method further includes determining an amount of lignin in the material using the measured second light. The ultraviolet wavelengths/wavelength bands could include at least one wavelength between 260 nanometers and 300 nanometers, inclusive (such as 280 nm). The one or more ultraviolet wavelengths/wavelength bands could additionally include 205 nanometers, 250 nanometers, 300 nanometers, and/or 360 nanometers. The method could also include illuminating the material using third light and measuring fourth light from the material, where the fourth light is based on the third light. The third light is associated with at least one wavelength/wavelength band that falls within a non-absorption wavelength band of lignin.

21 Claims, 4 Drawing Sheets

OTHER PUBLICATIONS

C. I. Thomson et al., "Excitation Energy Transfer in Lignin: Fluorescence of Kraft Residual Lignin," 2004, 1 page.

S. Katuscak et al., "The Effect of Paper Degradation on Uncertainty of Determination of Initial Lignin Content," 2006, 3, pp. 69-72.

D.P. Koullas et al., "Fluorescence Spectroscopy for the Characterisation of Lignocellulosics—An Overview of the Recent Research," National Technical University of Athens, Bioresource Technology Unit, 2004, 57 pages.

Bo Albinsson et al., "The Origin of Lignin Fluorescence," Journal of Molecular Structure 508 (1999), pp. 19-27.

Tarja T. Shakespeare et al., "Apparatus and Method for Camera-Based Color Measurements", U.S. Appl. No. 12/017,469, filed Jan. 22, 2008.

Tarja T. Shakespeare et al., "Apparatus and Method for Measuring and/or Controlling Ultraviolet-Activated Materials in a Paper-Making Process", U.S. Appl. No. 12/017,497, filed Jan. 22, 2008.

* cited by examiner

APPARATUS AND METHOD FOR MEASURING AND/OR CONTROLLING PAPER PULP PROPERTIES

TECHNICAL FIELD

This disclosure relates generally to measurement and/or control systems and more specifically to an apparatus and method for measuring and/or controlling paper pulp properties.

BACKGROUND

Paper, cardboard, and many other products are formed using pulp fibers, such as wood, straw, bamboo, or seed fibers. Wood fibers and other vascular plant fibers typically contain cellulose, hemicellulose, extractives, and lignin. Extractives typically include substances such as resin acids, fatty acids, turpenoid compounds, and alcohols. A bleaching process is typically used to remove at least some of the lignin and extractives from these fibers. The amount of lignin and extractives removed typically varies with the type of product being formed. For example, writing paper typically contains very little lignin, while cardboard typically contains more lignin.

The effectiveness of a bleaching process is traditionally determined using brightness measurements as defined by the International Organization for Standardization (ISO). The brightness measurements often involve measuring the reflectance of a finished product at a central wavelength of 457 nanometers (in the visible light spectrum).

SUMMARY

This disclosure provides an apparatus and method for measuring and/or controlling paper pulp properties.

In a first embodiment, a method includes illuminating a material using a first light. The first light is associated with one or more ultraviolet wavelengths or wavelength bands, and the material includes pulp fibers. The method also includes measuring a second light from the material, where the second light is based on the first light. In addition, the method includes determining an amount of lignin in the material using the measured second light.

In particular embodiments, the one or more ultraviolet wavelengths or wavelength bands include at least one wavelength between 260 nanometers and 300 nanometers, inclusive. For example, the one or more ultraviolet wavelengths or wavelength bands could include 280 nanometers. The one or more ultraviolet wavelengths or wavelength bands could additionally include 205 nanometers, 250 nanometers, 300 nanometers, and/or 360 nanometers.

In other particular embodiments, measuring the second light includes measuring the second light at one or more second ultraviolet wavelengths or wavelength bands. The one or more second ultraviolet wavelengths or wavelength bands could include at least one fluorescent emission wavelength or wavelength band associated with lignin.

In yet other particular embodiments, the method also includes illuminating the material using third light and measuring fourth light from the material, where the fourth light is based on the third light. Determining the amount of lignin in the material may include determining the amount of lignin in the material using the measured second light and the measured fourth light. The third light is associated with at least one wavelength or wavelength band that falls within a non-absorption wavelength band of lignin.

In still other particular embodiments, the method also includes adjusting a bleaching process performed on the pulp fibers and/or adjusting one or more additional materials added to the pulp fibers based on the determined amount of lignin in the material.

In additional particular embodiments, illuminating the material includes illuminating the material through a window in a pipe. Also, the second light reflects off of the material and travels through the window.

In a second embodiment, an apparatus includes one or more light emitting diodes configured to illuminate a material using a first light. The first light is associated with one or more ultraviolet wavelengths or wavelength bands, and the material includes pulp fibers. The apparatus also includes one or more detectors configured to measure a second light from the material, where the second light is based on the first light. The apparatus further includes a controller configured to determine an amount of lignin in the material using the measured second light.

In a third embodiment, a system includes a pulp production system configured to produce pulp and/or a stock preparation system configured to produce stock for a paper machine. The pulp or stock includes pulp fibers. The system also includes a sensor arrangement configured to illuminate a portion of the pulp or stock using a first light, where the first light is associated with one or more ultraviolet wavelengths or wavelength bands. The sensor arrangement is also configured to measure a second light from the pulp or stock and to determine an amount of lignin in the pulp or stock using the measured second light, where the second light is based on the first light.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1A through 3, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1A:
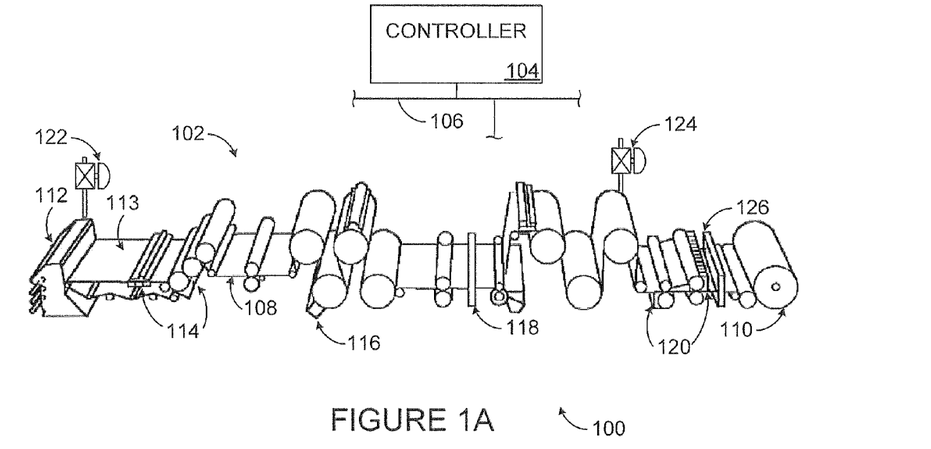
FIGS. 1A and 1B illustrate an example paper production system according to this disclosure.
Figure 1B:
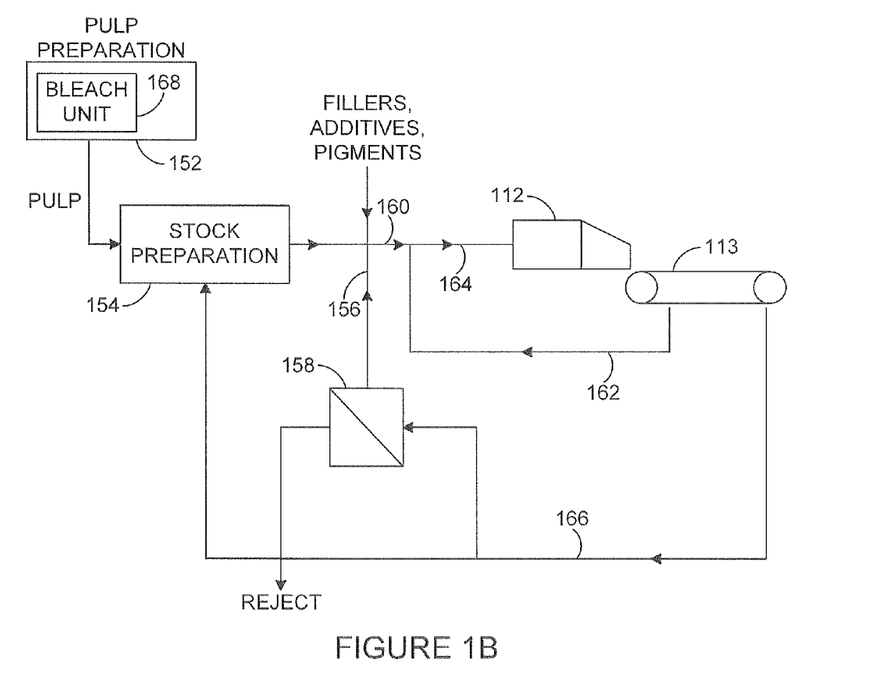

FIGS. 1A and 1B illustrate an example paper production system 100 according to this disclosure. The embodiment of the paper production system 100 shown in FIGS. 1A and 1B is for illustration only. Other embodiments of the paper production system 100 may be used without departing from the scope of this disclosure.

As shown in FIG. 1A, the paper production system 100 includes a paper machine 102, a controller 104, and a network 106. The paper machine 102 includes various components used to produce a paper product. In this example, the various components may be used to produce a paper sheet 108 collected at a reel 110. The controller 104 monitors and controls the operation of the paper machine 102 (as well as components in a wet-end of the papermaking process as shown in FIG. 1B), which may help to maintain or increase the quality of the paper sheet 108 produced in the system 100.

In this example, the paper machine 102 includes a headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water or a suspension of different composition into the pulp suspension across the sheet. The dilution water may be used to help ensure that the resulting paper sheet 108 has a more uniform basis weight or more uniform composition across the sheet 108. The headbox 112 may also include an array of slice lip actuators, which controls a slice opening across the machine from which the pulp suspension exits the headbox 112 onto the moving wire screen or mesh 113. The array of slice lip actuators may also be used to control the basis weight of the paper or the distribution of fiber orientation angles of the paper across the sheet 108.

An array of drainage elements 114, such as vacuum boxes, removes as much water as possible. An array of steam actuators 116 produces hot steam that penetrates the paper sheet 108 and releases the latent heat of the steam into the paper sheet 108, thereby increasing the temperature of the paper sheet 108 in sections across the sheet. The increase in temperature may allow for easier removal of water from the paper sheet 108. An array of rewet shower actuators 118 adds small droplets of water (which may be air atomized) onto one or both surfaces of the paper sheet 108. The array of rewet shower actuators 118 may be used to control the moisture profile of the paper sheet 108, reduce or prevent over-drying of the paper sheet 108, correct any dry streaks in the paper sheet 108, or enhance the effect of subsequent surface treatments (such as calendering).

The paper sheet 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper sheet 108 and transfers heat energy to it. The arrays of induction heating actuators 120 may therefore be used to control the caliper (thickness) profile of the paper sheet 108. The nips of a calender may also be equipped with other actuator arrays, such as arrays of air showers or steam showers, which may be used to control the gloss profile or smoothness profile of the paper sheet.

Two additional actuators 122-124 are shown in FIG. 1A. A thick stock flow actuator 122 controls the consistency of the incoming stock received at the headbox 112. A steam flow actuator 124 controls the amount of heat transferred to the paper sheet 108 from drying cylinders. The actuators 122-124 could, for example, represent valves controlling the flow of stock and steam, respectively. These actuators may be used for controlling the dry weight and moisture of the paper sheet 108. Additional components could be used to further process the paper sheet 108, such as a supercalender (for improving the paper sheet's thickness, smoothness, and gloss) or one or more coating stations (each applying a layer of coatant to a surface of the paper to improve the smoothness and printability of the paper sheet). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process the produced paper or with systems that produce or process other items or materials formed using pulp.

In order to control the paper-making process, one or more properties of the paper sheet 108 may be continuously or repeatedly measured. The sheet properties can be measured at one or various stages in the manufacturing process. This information may then be used to adjust the paper machine 102, such as by adjusting various actuators within the paper machine 102. This may help to compensate for any variations of the sheet properties from desired targets, which may help to ensure the quality of the sheet 108.

As shown in FIG. 1A, the paper machine 102 includes a scanner 126, which may include one or more sensors. The scanner 126 is capable of scanning the paper sheet 108 and measuring one or more characteristics of the paper sheet 108. For example, the scanner 126 could include sensors for measuring the weight, moisture, caliper (thickness), gloss, color, smoothness, or any other or additional characteristics of the paper sheet 108. The scanner 126 includes any suitable structure or structures for measuring or detecting one or more characteristics of the paper sheet 108, such as sets or arrays of sensors.

The controller 104 receives measurement data from the scanner 126 and uses the data to control the paper machine 102. The controller 104 could also receive measurement data from various components in the wet-end of the papermaking system as shown in FIG. 1B, such as components used for pulp preparation and/or stock preparation. The controller 104 could use this data to control the pulp and stock preparation processes and to control the paper machine 102. For example, the controller 104 may use the measurement data to adjust the various actuators in the paper machine 102 so that the paper sheet 108 has properties at or near desired properties. The controller 104 includes any hardware, software, firmware, or combination thereof for controlling the operation of at least part of the paper machine 102.

The network 106 facilitates communication between components of the system 100 (including components in FIG. 1A and in FIG. 1B). The network 106 represents any suitable network or combination of networks facilitating communication between components in the system 100. The network 106 could, for example, represent an Ethernet network, an electrical signal network (such as a HART or FOUNDATION FIELDBUS network), a pneumatic control signal network, or any other or additional network(s).

The stock provided to the headbox 112 can be produced as shown in FIG. 1B. Here, pulp is produced or prepared in a pulp preparation unit 152. The pulp preparation unit 152 could, for example, receive dry pulp and mix the dry pulp with water or other materials. The pulp preparation unit 152 could also receive pulp directly from a mill or other source. The pulp preparation unit 152 includes any suitable structure(s) for producing or preparing pulp for use in a paper or other machine.

The pulp is then provided to a stock preparation unit 154. In this embodiment, the stock preparation unit 154 processes the pulp to prepare the pulp for use in making the sheet 108. For example, the stock preparation unit 154 could clean and refine the pulp fibers so that the pulp fibers have desired properties. The stock preparation unit 154 could also receive and process recycled fibers recovered from the screen or mesh 113. The stock preparation unit 154 includes any suitable structure(s) for preparing fibers or other materials for use in a paper or other machine. For example, the stock preparation unit 154 could include sensors, such as sensors for pulp brightness, pH, and conductivity measurements.

The fibers provided by the stock preparation unit 154 are mixed with one or more fillers, additives, pigments, or other materials and with recycled materials 156 provided by a retention unit 158. The resulting mixture represents a thick stock 160 and has a relatively high fiber consistency (such as around 4%). The thick stock 160 is then mixed with white water in a short circulation path 162 to produce a thin stock 164. The thin stock 164 has a relatively low fiber consistency (such as around 0.2%). The thin stock 164 is provided to the headbox 112 for use in forming the sheet 108. A long circulation path 166 provides recycled material to the retention unit 158 and the stock preparation unit 154 for recovery. The retention unit 158 may also reject some of the material provided through the long circulation path 166.

In some embodiments, the light absorption of a finished product (such as the paper sheet 108) in the wavelength band between 260-300 nanometers can affect several properties of the product in the presence of ultraviolet light, such as the color or aging of the product. One way to control the light absorption of a product in this wavelength band is through bleaching. Bleaching reduces the amount of lignin and extractives in the pulp fibers, and the amount of lignin and extractives present in the finished product affects the product's light absorption in the 260-300 nm band. The light absorption in any wavelength band affects the reflectance and transmittance in that band. Accordingly, at least one of the components in the system 100 includes a bleaching unit 168 (which in this example is located in the pulp preparation unit 152).

The bleaching unit 168 here is used to bleach the pulp fibers to reduce the amount of lignin and extractives in the pulp. The amount of bleaching performed by the bleaching unit 168 could be based on the product to be formed in the system 100. The bleaching unit 168 could use any suitable technique(s) for removing lignin and extractives from pulp fibers, such as oxygen delignification, hydrogen peroxide extraction and bleaching, chlorine and chlorine dioxide beaching, or any other or additional bleaching or delignification process(es). The bleaching unit 168 includes any suitable structure(s) for removing lignin and extractives from pulp fibers. For example, the bleaching unit 168 could include sensors, such as sensors for pulp brightness, consistency, pH, and conductivity measurements.

As noted above, ISO brightness measurements often involve measuring the reflectance of a finished product at a central wavelength of 457 nm. However, this selected wavelength band for the ISO brightness measurements is not at the maximum absorption band of lignin. More information of lignin's absorption properties (as well as the absorption properties of the extractives) is available in the ultraviolet band of light. This information can also be linked with the aging properties of the paper product.

As described more fully below, a sensor arrangement can be used to determine one or more properties of pulp after the bleaching process. The properties of the pulp can be determined by illuminating the pulp with ultraviolet light at one or more ultraviolet wavelengths or wavelength bands and measuring the radiances reflected from, transmitted through, or emitted by the pulp. The measured radiances can then be used, for example, to determine one or more properties of the pulp, such as reflectance, fluorescence, and absorption properties of cellulose and lignin in the pulp. This technique can also be used to analyze any residual fluorescent whitening agents (FWAs) in recycled fibers. If the properties of the pulp are outside desired values or ranges, the bleaching process can be adjusted, such as by changing the chemical dosage and chemical type used in the bleaching process. As a result, the bleaching process in the bleaching unit 168 can be more accurately controlled.

Other or additional actions may also occur if the properties of the pulp are outside desired values or ranges. These actions could include adjusting the fillers, additives, pigments, FWA killers, or other materials added to the stock produced by the stock preparation unit 154. Also, the pulp could be rejected and not used to produce the paper sheet 108, or the operation of the paper machine 102 could be adjusted based on the identified properties of the pulp. In other words, various actions can occur when measured radiances of the pulp are not satisfactory or acceptable. Because of this, greater control is provided for ensuring that the finished product being produced satisfies various requirements, such as color or aging requirements.

Although FIGS. 1A and 1B illustrate one example of a paper production system 100, various changes may be made to FIGS. 1A and 1B. For example, other systems could be used to produce paper products or other products. Also, while shown as including a single paper machine 102 with various components and a single controller 104, the production system 100 could include any number of paper machines or other production machinery having any suitable structure, and the system 100 could include any number of controllers. As a particular example, the controller 104 could monitor and control the operation of the pulp preparation 152 and the stock preparation unit 154, or these units may have their own controller(s). Further, any other or additional components could be used for preparing the stock used by the paper machine 102 to produce the sheet 108. In addition, FIGS. 1A and 1B illustrate one operational environment in which measurement and control of paper pulp's properties can be used. This functionality could be used in any other suitable system.

FIGS. 2A through 2D illustrate an example mechanism for measuring and controlling paper pulp properties according to this disclosure. The embodiments of the mechanism shown in FIGS. 2A through 2D are for illustration only. Other embodiments of the mechanism could be used without departing from the scope of this disclosure. Also, for ease of explanation, the mechanism shown in FIGS. 2A through 2D is described with respect to the system 100 shown in FIGS. 1A and 1B. The mechanism could be used in any other suitable system.

As shown in FIGS. 2A through 2D, the measuring and controlling mechanism includes one or more light emitting diodes (LEDs) 202, which are capable of generating light at one or more wavelengths or wavelength bands. The light is used to illuminate a material (such as pulp or paper) being examined. For example, the light emitting diodes 202 could emit ultraviolet light at any suitable wavelengths or wavelength bands, including in the UV(A), UV(B), and/or UV(C) bands. As particular examples, one or more of the light emitting diodes 202 could emit ultraviolet light having one or more of the following wavelengths: 205 nm, 250 nm, 280 nm, 300 nm, 360 nm, and 380 nm. The light emitting diodes 202 could also emit light having one or more reference wavelengths or wavelength bands, such as one to four reference wavelengths within the ultraviolet and/or visible bands. Example reference wavelengths/bands could include one reference wavelength or wavelength band in the UV(B) band and others in the red or yellow visible spectrum. The reference wavelengths or wavelength bands may exist within at least one non-absorption wavelength or wavelength band of lignin or FWAs, thereby allowing reference measurements to be taken of the material being examined. The light emitting diodes 202 could represent any suitable number and type of light emitting diode(s) for generating light at any suitable wavelengths or wavelength ranges, including regular LEDs, organic LEDs (OLEDs), and flashing LEDs (FLEDs).

An LED controller 204 is coupled to and controls the operation of the light emitting diodes 202. For example, the LED controller 204 could turn the light emitting diodes 202 on and off and vary the current provided to the light emitting diodes 202. The LED controller 204 could also control the cooling of the light emitting diodes 202 or any other or additional aspects of the light emitting diodes' operation. Depending on the implementation, the LED controller 204 could further control the wavelength or wavelength band of the light emitted by the light emitting diodes 202. The LED controller 204 includes any suitable structure for controlling one or more light emitting diodes.

Optics 206 can be used to control the illumination of the material being examined. The optics 206 could, for example, focus the emitted light from the light emitting diodes 202 onto the material or diffuse the emitted light. The optics 206 include any suitable structure(s) for controlling the illumination of the material, such as one or more lenses, mirrors, or diffusers. Similarly, optics 208 can be used to control radiances reflected from the material being examined, such as by focusing the radiances. The optics 208 include any suitable structure(s), such as one or more lenses, mirrors, or diffusers.

One or more detectors 210 measure the radiances reflected or otherwise provided by the material being examined. For example, the detectors 210 could measure the intensity of the radiances at certain ultraviolet or other wavelengths or wavelength bands. As a particular example, one or more detectors 210 could measure the intensity of ultraviolet light having one or more of the following wavelengths: 205 nm, 250 nm, 280 nm, 300 nm, 360 nm, and 380 nm. If the material being examined includes a fluorescent material, one or more detectors 210 could also measure the intensity of light at the fluorescent material's emission wavelength(s), such as 440 nm. One or more detectors 210 could further measure the intensity of reference light, such as wavelengths in UV(B) and/or the red or yellow visible spectrum. The measurement(s) of the reference light could occur using light reflected from the material being examined or by directly sampling the reference light emitted by the light emitting diodes 202. A detector 210 could measure the intensity of light at one or multiple wavelengths or wavelength bands.

In some embodiments, at least one detector 210 measures light from pulp being examined at the same wavelengths as the light emitted by the light emitting diodes 202, as well as at higher wavelengths associated with fluorescence emissions by components of the pulp (which could be produced by FWAs or lignin). For example, at least one detector 210 could have a detection wavelength band at an excitation band of lignin (such as 280 nm) and possibly a fluorescent emission band of lignin (such as 360 nm and/or 410 nm) with illumination by light emitting diode(s) at the excitation band of lignin. In particular embodiments, between two and five ultraviolet wavelengths or wavelength bands can be emitted and measured (one of which is between 260 nm and 300 nm, such as 280 nm), and one to four reference wavelengths can be emitted and measured.

Each detector 210 includes any suitable structure or structures for measuring light. Each detector 210 could, for example, include a spectrometer covering an illumination wavelength or wavelength band and possibly a higher wavelength or wavelength band, a photomultiplyer tube with or without a band filter, or an LED detector. Also, different detectors 210 could be implemented using different components.

Control values for the light emitting diodes 202 can be provided by a controller 212, and measurements from the detectors 210 can be provided to the controller 212. The controller 212 may, among other things, use measurements from the detectors 210 to determine one or more properties of the material being examined (such as pulp being provided to the paper machine 102). The controller 212 could use these determined properties to estimate the quality of and make adjustments to a bleaching process, thereby adjusting the one or more properties of the pulp. The controller 212 could also make adjustments to materials added to the pulp, thereby adjusting the composition of the stock provided to the paper machine 102. In addition, the controller 212 could reject pulp or stock material (prevent it from being used by the paper machine 102), or the controller 212 could adjust the operation of the paper machine 102 to compensate for variations in the pulp properties.

The controller 212 could perform any other or additional actions, such as estimating the aging properties of a finished product utilizing at least one measured ultraviolet absorption band of the lignin, analyzing types of lignin structures to determine partial least squares (PLS) or other models for paper aging, and estimating optical properties for ultraviolet-excited chemicals (such as FWAs). The controller 212 could perform any other or additional functions using measurements related to the properties of pulp or other material.

The controller 212 includes any hardware, software, firmware, or combination thereof for using measurements related to the properties of pulp or other material. In this example, the controller 212 includes at least one processor 214 and at least one memory 216 for storing instructions and data used, generated, or collected by the processor(s) 214. The controller 212 also includes at least one network interface 218 for communicating over a network, such as an Ethernet network or an electrical signal network. The controller 212 in this example could be implemented as part of the process controller 104 in FIG. 1A, integrated into another component in the system 100, or used as a stand-alone component in the system 100.

The sensor arrangement formed using the components 202-212 can be used in different ways as shown in FIGS. 2A through 2D. For example, in FIG. 2A, the sensor arrangement is used to measure one or more properties of a sample 219 of material. The sample 219 could, for example, represent a sample of pulp produced by the pulp preparation unit 152 or a sample of stock produced by the stock preparation unit 154. The sample 219 could be prepared in any suitable manner, such as by removing the sample 219 from a tank or other storage vessel. The sample 219 could also be prepared in an "off-line" manner (outside of the normal process flow). This could include placing the pulp material between layers of material having the same or lower moisture content, forming a pancake-type structure. The sample 219 could be obtained or produced in any other suitable manner.

Figure 2A:
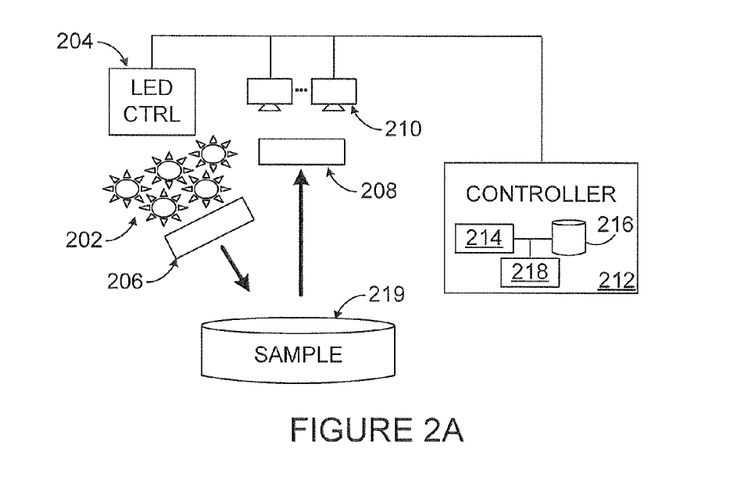
FIGS. 2A through 2D illustrate an example mechanism for measuring and controlling paper pulp properties according to this disclosure.
Figure 2B:
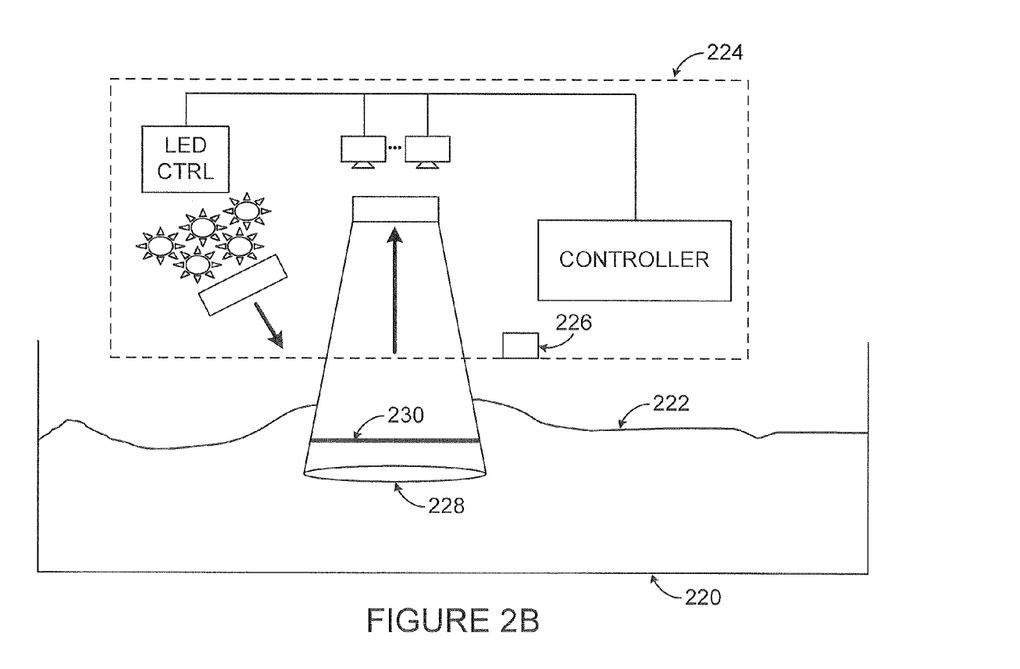

In FIG. 2B, the sensor arrangement is used in conjunction with a tank 220 containing material 222, such as a tank storing bleached pulp waiting for subsequent use or other suitable process location in the bleaching process. In some embodiments, at least some of the components 202-212 could be integrated into a gauge 224 or other instrument that can be placed within the tank 220. In order to help improve measurements, various techniques could be used to compensate for the waves or other disturbances to the surface of the material 222 in the tank 220. For example, a distance sensor 226 could be used to identify the distance between the gauge 224 and the measured surface of the material 222. The identified distance could then be used to compensate for measurements taken by the gauge 224 or to move the gauge 224 within the tank 220 (so that the gauge 224 is at a specified distance from the material 222). As another example, the gauge 224 could include a cup-type structure or other enclosure 220 in which higher-pressure air can be used to control the distance between other gauge components and a controlled surface 230 of the material 222. In particular embodiments, an air bubble within the enclosure 228 can be periodically reformed, which can (among other things) allow a new measurement surface 230 to be reformed from time to time. In this way, additional measurement windows (which can get dirty and disturb the measurements) are not needed.

Figure 2C:
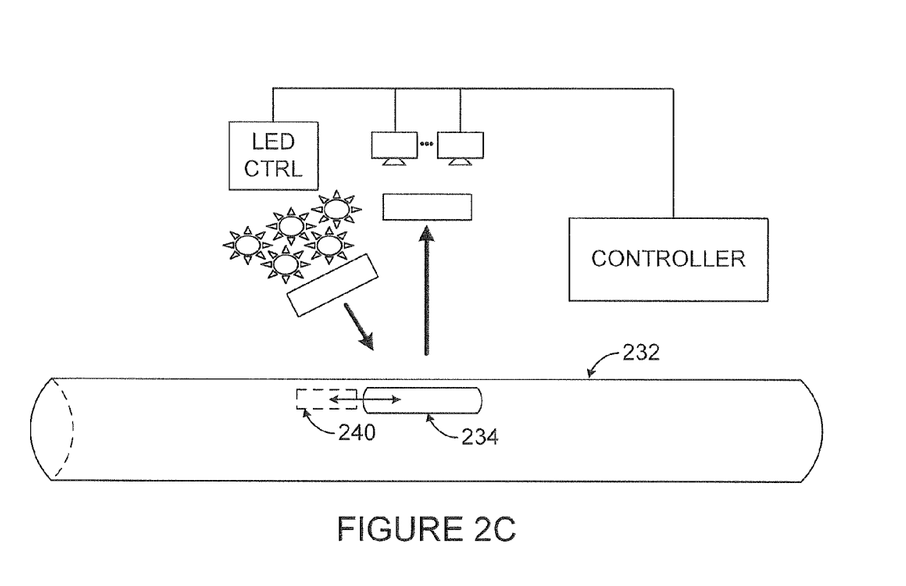

In FIG. 2C, the sensor arrangement is used in conjunction with a pipe 232, which transports pulp and possibly other material from one location to another within the system 100. For example, the sensor arrangement could take measurements of stock flowing through the pipe 232 through a window 234 in the pipe 232. The window 234 could be formed from any suitable material facilitating illumination and measurement of the material in the pipe 232. The window 234 could, for example, represent UV quartz, or LEDs could be manufactured on the window 234 with or without required optics for picking up the reflected and/or emitted radiances from the material.

Figure 2D:
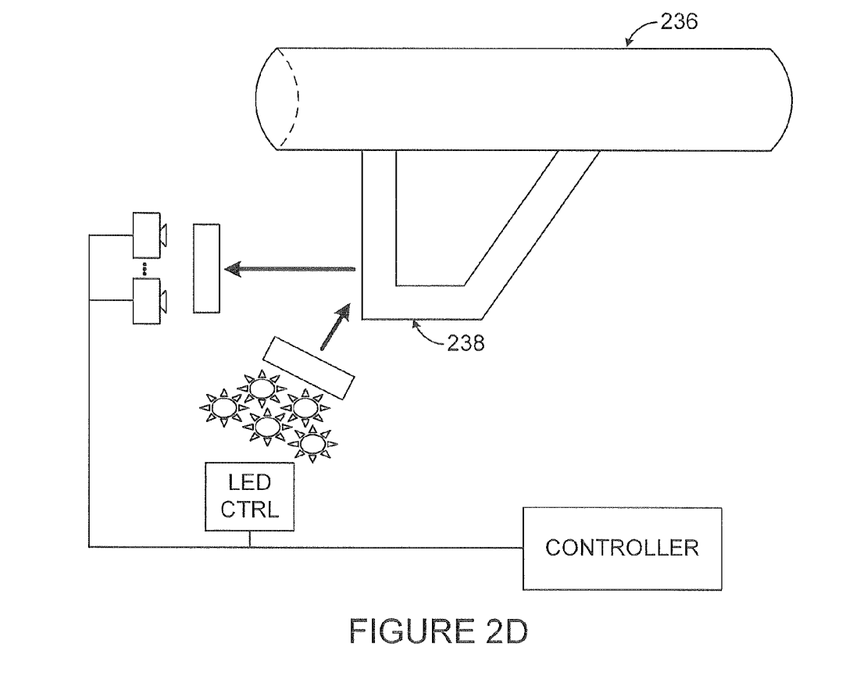

In FIG. 2D, the sensor arrangement is again used in conjunction with a pipe 236, and the sensor arrangement takes measurements of material flowing through a sampling pipe 238 (which branches away from and then rejoins the main pipe 236). Again, a window or other structure could be used to allow measurement of the material in the sampling pipe 238.

In any of these embodiments, the sensor arrangement can be used to take any suitable measurements of pulp (with or without other material) and to determine one or more properties of the pulp (such as properties of the pulp's lignin or cellulose). For example, the sensor arrangement could illuminate the pulp with ultraviolet light at one or more wavelengths or wavelength bands. The sensor arrangement could also illuminate the pulp with light at one or more reference wavelengths or wavelength bands. The sensor arrangement could further take various measurements of light from the pulp, such as at the same wavelengths or wavelength bands as the light emitted by the light emitting diodes 202 and at any wavelengths or wavelength bands associated with fluorescence of the pulp (such as fluorescence of the lignin in the pulp and/or FWAs in the pulp). Based on these measurements, the controller 212 can perform any suitable calculations. For instance, the controller 212 could determine ratios between the light measurements for various ones of the different wavelengths or wavelength bands. These ratios can be used to identify or estimate the content of lignin in the pulp being examined. In this way, determinations can be made regarding the quality of the bleaching process used to remove lignin from pulp. This can also be used to make adjustments to the bleaching process, to reject the pulp, to control the additional materials mixed with the pulp, to control the paper machine 102, or in any other suitable manner.

It can be noted that the light emitting diodes 202 and the detectors 210 can be arranged in any suitable manner, such as by arranging each in a circle. Also, the light emitting diodes 202 could illuminate a material being examined and the detectors 210 could measure light from the material being examined at any suitable geometry. For example, the illumination could be at 45° and the detection could be at 0° (denoted 45/0), the illumination could be at 0° and the detection could be at 0° (denoted 0/0), or the illumination could be between 0-45° and the detection could be between 0-45° (denoted 0-45/0-45). During illumination, one or multiple light emitting diodes 202 can be turned on at the same time. In particular embodiments, the light emitting diodes 202 could be pulsed randomly in a cycle and all have constant illumination power. In other particular embodiments, the light emitting diodes 202 could be pulsed randomly in a cycle and have varying illumination powers.

In some embodiments, the detectors 210 can be calibrated to ensure proper operation of the sensor arrangement. This may allow, for example, the controller 212 to determine a baseline for measurements made by the detectors 210. The calibration could occur in any suitable manner, such as by using a calibration tile or temporary sample to modify the illumination path in order to measure the light emitting diodes' irradiance energy. The calibration tile could include different areas with known reflectances at specific wavelengths or wavelength bands. The calibration tile could be illuminated using one or more of the light emitting diodes 202, and measurements of the calibration tile could be taken using the detectors 210. In this way, the controller 212 can determine how the detectors 210 operate given specific illumination of a surface with known reflectances.

One specific use of the calibration tile is shown in FIG. 2C. Here, a configuration tile 240 resides in and can be moved back and forth within the pipe 232. This may allow, for example, the calibration tile 240 to be moved into the window 234 for calibration of the sensor arrangement and then moved out of the window 234 for measurement of material in the pipe 232. However, it may be noted that the calibration tile 240 could be used in any other suitable manner. For instance, the calibration tile 240 could reside outside of the pipe 232 and be manually or automatically placed above the window 234. The calibration tile 240 could also be used in any of the other embodiments of the sensor arrangement shown in FIGS. 2A through 2D.

Although FIGS. 2A through 2D illustrate one example of a mechanism for measuring and controlling paper pulp properties, various changes may be made to FIGS. 2A through 2D. For example, the sensor arrangement could be used in any other configuration and is not limited to use with just samples, tanks, and pipes. Also, the sensor arrangement could include any number of light emitting diodes, detectors, controllers, optics, or any other or additional components. In addition, the functional division shown in FIGS. 2A through 2D is for illustration only. Various components in each figure could be combined, subdivided, or omitted and additional components could be added according to particular needs.

Figure 3:
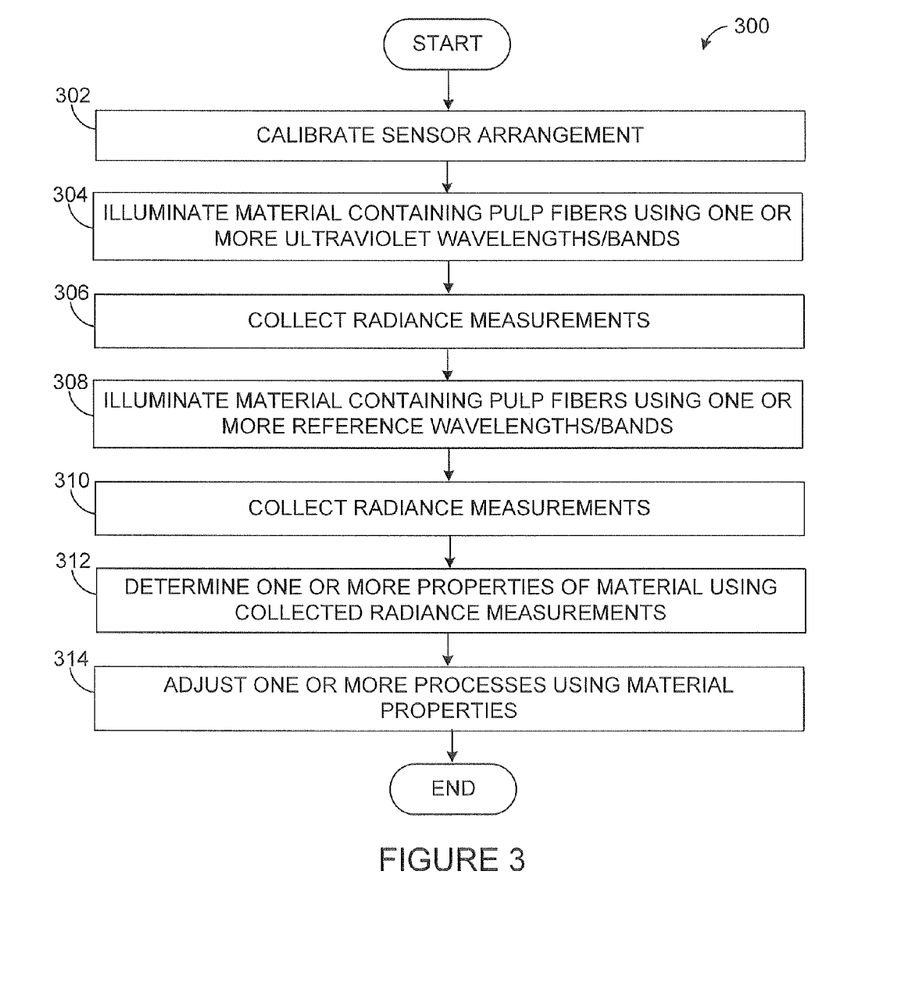
FIG. 3 illustrates an example method for measuring and controlling paper pulp properties according to this disclosure.

FIG. 3 illustrates an example method 300 for measuring and controlling paper pulp properties according to this disclosure. The embodiment of the method 300 shown in FIG. 3 is for illustration only. Other embodiments of the method 300 could be used without departing from the scope of this disclosure.

A sensor arrangement is calibrated at step 302. This could include, for example, placing a calibration tile in a position so that the tile can be illuminated using one or more light emitting diodes 202 using specific wavelengths or wavelength bands of light. This may also include using one or more detectors 210 to detect the light from areas of known reflectances on the calibration tile. This may further include providing the detector measurements to the controller 212, which can use the measurements to establish baseline readings for the detectors 210 or to identify how to adjust readings from the detectors 210.

A material containing pulp fibers is illuminated using ultraviolet light at one or more wavelengths or wavelength bands at step 304. This could include, for example, one or more of the light emitting diodes 202 generating ultraviolet light at one or more ultraviolet wavelengths or wavelength bands. As a particular example, one or multiple light emitting diodes 202 could sequentially generate ultraviolet light at wavelengths of 205 nm, 250 nm, 280 nm, 300 nm, 360 nm, and 380 nm.

Radiance measurements are collected from the material at step 306. This could include, for example, one or more of the detectors 210 measuring the intensity of light reflected from the material at specified wavelengths or wavelength bands. As a particular example, one or multiple detectors 210 could sequentially measure light reflected from the material at wavelengths of 205 nm, 250 nm, 280 nm, 300 nm, 360 nm, and 380 nm. One or multiple detectors 210 could also measure light at any emission wavelengths associated with fluorescent material, such as fluorescence whitening agents. As an example, a fluorescent material could have a maximum excitation wavelength of 280 nm or 360 nm and a maximum emission wavelength of 440 nm. One or multiple fluorescent materials could also have a cascade effect, such as when one fluorescent material is excited at 280 nm and emits at 360 nm and the same or different fluorescent material is excited at 360 nm and emits at 440 nm. Any of these wavelengths or wavelength bands can be measured by the one or more of the detectors 210.

The material is illuminated using reference light at one or more reference wavelengths or wavelength bands at step 308. This could include, for example, one or more of the light emitting diodes 202 generating light at one or more wavelengths or wavelength bands in the visible spectrum, such as in a UV band and/or in the red or yellow visible spectrum. Radiance measurements are collected from the material at step 310. This could include, for example, one or more of the detectors 210 measuring the intensity of light reflected from the material at specified wavelengths or wavelength bands. The specified wavelengths or wavelength bands could be the same specified wavelengths or wavelength bands used by the light emitting diodes 202 at step 308.

One or more properties of the material are determined at step 312, and one or more processes are adjusted using the determined properties at step 314. This may include, for example, the controller 212 using the measured radiances to determine a quantity of lignin in the pulp. This may allow the controller 212 to estimate the effectiveness of a bleaching process and to make adjustments to the bleaching process in order to obtain a desired result (such as a desired quantity of lignin). This may also allow the controller 212 to reject the pulp, adjust the materials mixed with the pulp, or adjust the paper machine 102 to compensate for variations in the pulp. The properties of the material can be determined in any suitable manner, such as by using one or more ultraviolet measurements and one or more reference measurements to determine the quantity of lignin in the pulp.

Although FIG. 3 illustrates one example of a method 300 for measuring and controlling paper pulp properties, various changes may be made to FIG. 3. For example, while shown as a series of steps, various steps in FIG. 3 could overlap, occur in parallel, occur in a different order, or occur multiple times.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
    illuminating a material using a first light, the first light associated with one or more ultraviolet wavelengths or wavelength bands, the material comprising pulp fibers;
    illuminating the material using a second light, wherein the second light is associated with at least one non-absorption wavelength or wavelength band of lignin;
    measuring a third light from the material, the third light based on the first light;
    measuring a fourth light from the material, the fourth light based on the second light; and
    determining an amount of lignin in the material using the measured third light and the measured fourth light.

2. The method of claim 1, wherein the one or more ultraviolet wavelengths or wavelength bands include at least one wavelength between 260 nanometers and 300 nanometers, inclusive.

3. The method of claim 2, wherein the one or more ultraviolet wavelengths or wavelength bands include 280 nanometers.

4. The method of claim 3, wherein the one or more ultraviolet wavelengths or wavelength bands further include at least one of: 205 nanometers, 250 nanometers, 300 nanometers, and 360 nanometers.

5. The method of claim 1, wherein measuring the third light comprises measuring the third light at one or more second ultraviolet wavelengths or wavelength bands.

6. The method of claim 5, wherein the one or more second ultraviolet wavelengths or wavelength bands include at least one fluorescent emission wavelength or wavelength band associated with lignin.

7. The method of claim 1, wherein the second light comprises light within at least one of: a UV(B) band, a red visible spectrum, and a yellow visible spectrum.

8. The method of claim 1, further comprising:
adjusting a bleaching process performed on the pulp fibers based on the determined amount of lignin in the material.

9. The method of claim 1, further comprising:
adjusting one or more additional materials added to the pulp fibers based on the determined amount of lignin in the material.

10. The method of claim 1, wherein:
illuminating the material comprises illuminating the material through a window in a pipe; and
the second light reflects off of the material and travels through the window.

11. An apparatus comprising:
one or more light emitting diodes configured to illuminate a material using a first light and a second light, the first light associated with one or more ultraviolet wavelengths or wavelength bands, the second light associated with at least one non-absorption wavelength or wavelength band of lignin, the material comprising pulp fibers;
one or more detectors configured to measure a third light from the material and to measure a fourth light from the material, the third light based on the first light, the fourth light based on the second light; and
a controller configured to determine an amount of lignin in the material using the measured third light and the measured fourth light.

12. The apparatus of claim 11, wherein the one or more ultraviolet wavelengths or wavelength bands include at least one wavelength between 260 nanometers and 300 nanometers, inclusive.

13. The apparatus of claim 12, wherein the one or more ultraviolet wavelengths or wavelength bands include 280 nanometers.

14. The apparatus of claim 13, wherein the one or more ultraviolet wavelengths or wavelength bands further include at least one of: 205 nanometers, 250 nanometers, 300 nanometers, and 360 nanometers.

15. The apparatus of claim 11, wherein the one or more detectors are configured to measure the third light at one or more second ultraviolet wavelengths or wavelength bands.

16. The apparatus of claim 15, wherein the one or more second ultraviolet wavelengths or wavelength bands include at least one fluorescent emission wavelength or wavelength band associated with lignin.

17. The apparatus of claim 11, wherein the second light comprises light within at least one of: a UV(B) band, a red visible spectrum, and a yellow visible spectrum.

18. A system comprising:
at least one of: a pulp production system configured to produce pulp and a stock preparation system configured to produce stock for a paper machine, the pulp or stock comprising pulp fibers; and
a sensor arrangement configured to:
illuminate a portion of the pulp or stock using a first light and a second light, the first light associated with one or more ultraviolet wavelengths or wavelength bands, the second light associated with at least one non-absorption wavelength or wavelength band of lignin;
measure a third light and a fourth light from the pulp or stock, the third light based on the first light, the fourth light based on the second light; and
determine an amount of lignin in the pulp or stock using the measured third light and the measured fourth light.

19. The system of claim 18, wherein the second light comprises light within at least one of: a UV(B) band, a red visible spectrum, and a yellow visible spectrum.

20. The system of claim 18, wherein the sensor arrangement is further configured, based on the determined amount of lignin, to least one of:
adjust a bleaching process performed on the pulp fibers;
adjust one or more materials used to form the pulp or stock;
adjust the paper machine; and
reject the pulp or stock.

21. A method comprising:
causing at least one light emitting diode to illuminate a material using a first light, the first light associated with one or more ultraviolet wavelengths or wavelength bands, the material comprising pulp fibers;
causing the at least one light emitting diode to illuminate the material using a second light, wherein the second light is associated with at least one non-absorption wavelength or wavelength band of lignin;
receiving a measurement of a third light from the material, the third light based on the first light;
receiving a measurement of a fourth light from the material, the fourth light based on the second light; and
determining an amount of lignin in the material using the measurements of the third light and the fourth light.

* * * * *